(12) United States Patent
Revesz et al.

(10) Patent No.: US 6,175,016 B1
(45) Date of Patent: Jan. 16, 2001

(54) PYRIDINE DERIVATIVES

(75) Inventors: Laszlo Revesz, Therwil; Rudolf Waelchli, Basel, both of (CH)

(73) Assignee: Novartis AG, Basel (CH)

( * ) Notice: Under 35 U.S.C. 154(b), the term of this patent shall be extended for 0 days.

(21) Appl. No.: 08/281,887

(22) Filed: Jul. 28, 1994

Related U.S. Application Data

(63) Continuation-in-part of application No. 08/011,445, filed on Jan. 29, 1993, now abandoned.

(30) Foreign Application Priority Data

Jan. 31, 1992 (GB) ................................................ 9202139
Jul. 28, 1993 (GB) ................................................ 9315547

(51) Int. Cl.$^7$ ........................ C07D 213/08; C07D 213/14
(52) U.S. Cl. ........................ 546/250; 546/300; 546/323
(58) Field of Search .................................. 546/300, 323, 546/250

(56) References Cited

U.S. PATENT DOCUMENTS 4,973,666 * 11/1990 Eyre ..................................... 530/323

* cited by examiner

Primary Examiner—Dwayne C. Jones
(74) Attorney, Agent, or Firm—Hesna J. Pfeiffer

(57) ABSTRACT

The invention relates to a process for producing pyridinoline and deoxypyridinoline crosslinks and derivatives thereof and their use in determining connective tissue disorders in humans and animals.

8 Claims, No Drawings

PYRIDINE DERIVATIVES

The present application is a continuation-in-part of previously filed application Ser. No. 08/011,445 filed Jan. 29, 1993 abandoned on Aug. 23, 1994.

The present invention relates to pyridine derivatives, processes for their production and their use in diagnosis to detect bone and other connective tissue disorders in humans and animals.

Compounds of formula IA

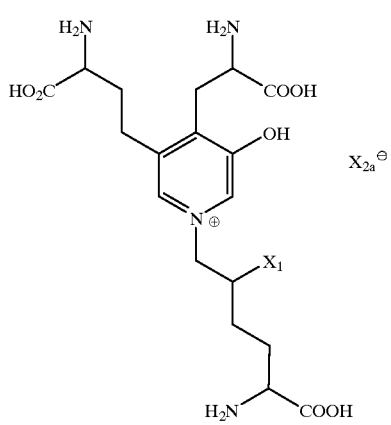

(IA)

wherein $X_1$ is H or OH, and $X_{2a}^{\ominus}$ is a chloride or acetate ion have been extracted from urine either by hydrolysis with 6M HCl at about 108° C. for approximately 24 hours (see Eyre et al., Ann. Rev. Biochem., 1984, 53, 717–748) or by chromatography using acetic acid as eluant (see D. R. Eyre et al. Anal. Biochem. 137, 380–388 (1984). Compounds of formula IA have been disclosed as an index of collagen degradation in metabolic bone and cartilage diseases based on the quantitating of their concentration in urine excretion over a fixed period (see Wu and Eyre, Biochemistry, 1984, 23, 1850; Robins et al., Analytical Biochem., 1988, 169, 197–203; D. Uebelhart et al., Bone and Mineral, 1990, 8, 87–96).

Interest in these compounds (referred to in literature as pyridinoline [$X_1$=OH] and deoxypyridinoline [$X_1$=H] crosslinks) as a marker for connective tissue metabolism abnormalities e.g. for measurements of bone resorption in human, is growing.

However, as the compounds of formula IA are until now natural compounds obtained by extraction, they do not meet the requirements for running standardized reproducible, reliable and non time-consuming assays.

There is a high need for defined standard pyridinoline crosslinks.

It is the purpose of the present invention to provide new pyridine derivatives and their production by chemical synthesis including the production of a compound of formula IA, in a substantially pure form in order to allow bone turn-over measurements under well standardized conditions.

More particularly, the present invention provides a compound of formula I

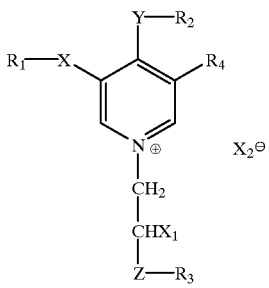

(I)

wherein each of X, Y and Z, independently is $C_{1-8}$alkyl; $C_{1-8}$alkyl interrupted by one or two heteroatoms selected from O, N and S; $C_{5-7}$cycloalkyl; $C_{5-7}$ cycloalkyl-C$_{1-4}$ alkyl; ($C_{1-4}$alkyl)-$C_{5-7}$cycloalkyl; ($C_{1-4}$alkyl)-$C_{5-7}$cycloalkylene-C 1-4 alkyl; optionally substituted aryl; optionally substituted heteroaryl; ($C_{1-4}$alkyl)-aryl; ($C_{1-4}$ alkyl)-heteroaryl; ($C_{1-4}$alkyl)-arylene-$C_{1-4}$ alkyl; ($C_{1-4}$alkyl)-heteroarylene-$C_{1-4}$ alkyl; aryl-$C_{1-4}$ alkyl; heteroaryl-$C_{1-4}$alkyl, the aryl or heteroaryl moieties of the above mentioned groups being optionally substituted;

$R_3$ is COOH or a functional derivative thereof; CHO; CN; $C_{1-8}$ alkoxy; $SO_2$; —$PO_3H$ or a functional derivative thereof; —$SO_3H$ or a functional derivative thereof; a primary, secondary or tertiary amino group; a saturated or unsaturated cyclic amino group; or a radical of formula (a)

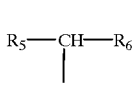

(a)

wherein $R_5$ is a primary, secondary or tertiary amino group or a saturated or unsaturated cyclic amino group, and $R_6$ is —COOH or a functional derivative thereof or —CO—$Y_2$-$R_9$ wherein $Y_2$ is a spacer and $R_9$ is a secondary amino group;

each of $R_1$ and $R_2$, independently, is hydrogen or has one of the significances given for $R_3$, $R_4$ is hydroxy; C 6alkoxy; or polyalkylenoxy;

$X_1$ is H or OH, and $X_2^{\ominus}$ is an anion with the proviso that i) when both X and Y comprise an alkyl moiety, the chain length of the alkyl moiety in —Y— is at least one carbon atom shorter than the alkyl moiety in —X—, and ii) $X_2$ is other than $Cl^{\ominus}$ or $CH_3COO^{\ominus}$ when each of —X—$R_1$ and —Z—$R_3$ is

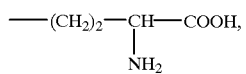

—Y—R$_2$ is

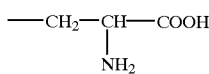

and R$_4$ is hydroxy.

C$_{1-8}$ alkyl is preferably C$_{1-6}$alkyl, more particularly C$_{1-4}$alkyl, especially C$_{1-2}$alkyl.

Preferably aryl means phenyl or 1- or 2-naphthyl, particularly phenyl. Aryl may be substituted, e.g. mono- di- or trisubstituted by hydroxy, C$_{1-4}$ alkyl, C$_{1-4}$alkoxy and/or halogen. Preferably aryl is unsubstituted or monosubstituted phenyl.

Preferably heteroaryl means a saturated or unsaturated 5- or 6-membered heterocyclic ring, e.g. imidazolyl, thiazolyl, piperidinyl, piperazinyl or phthaloyl. When substituted, it may be mono-, di- or trisubstituted by hydroxy, C$_{1-4}$alkyl, C$_{1-4}$ alkoxy and/or halogen. Preferably heteroaryl is unsubstituted.

When R$_1$, R$_2$, R$_3$ or R$_5$ is a secondary amino group, it is preferably —NHR$_a$ wherein R$_a$ is C$_{1-8}$alkyl; C$_{1-8}$alkyl optionally substituted by COOH or functional derivative thereof; C$_{2-8}$ alkenyl; C$_{3-7}$cycloalkyl; C$_{3-7}$cycloalkyl-C$_{1-8}$alkyl; phenyl; phenyl-C$_1$ alkyl; or R$_a$ is a radical —Y$_a$ or —Z$_a$—Y$_b$ wherein Y$_a$ is a protecting group or a group capable of covalently reacting with an antigen or a protecting group, Z$_a$ is a spacer and Y$_b$ is a protecting or antigenic group, biotinyl or a group derived from a molecule capable of forming a complex with another molecule like the biotin-avidin tool.

When R$_1$, R$_2$, R$_3$ or R$_5$ is a tertiary amino group, it is preferably —NR$_a$R$_a$' wherein R$_a$ is as defined above and R$_a$' has independently one of the significances given for R$_a$; preferably R$_a$ and R$_a$' are two substituents which do not hinder each other.

N-protecting groups as Y$_a$ or Y$_b$ include such groups as e.g. disclosed in "Protective Groups in Organic Synthesis", T. W. Greene, J. Wiley & Sons NY (1981), 219–287, for example acyl such as formyl, acetyl, trifluoroacetyl, methoxysuccinyl, hydroxysuccinyl or benzoyl optionally substituted on the phenyl ring with e.g. p-methoxycarbonyl, p-methoxy, p-nitro or p-phenylsulfonamidocarbonyl; alkoxycarbonyl such as t-butyloxycarbonyl, isobutyloxycarbonyl or methoxycarbonyl; allyl-oxycarbonyl; arylmethoxycarbonyl such as 9-fluorenylmethoxycarbonyl or benzyloxycarbonyl optionally substituted on the phenyl ring with p-methoxy, p-nitro, o- or p-chloro, m-phenyl or 3,4-dimethyl; trityl; arylmethyl such as benzyl optionally ring substituted with p-methoxy, p-nitro or p-chloro; or arylsulfonyl such as phenylsulfonyl optionally ring substituted with p-methyl or p-methoxy, or naphthylsulfonyl optionally ring substituted with e.g. amino or di(C$_{1-4}$alkyl)amino.

Examples of carboxylic acid functional derivatives are acid halides, acid anhydrides (including mixed acid anhydrides), active esters, active amides, etc. Among the acid halides, acid chloride is the most frequently used. Examples of the acid anhydrides include cyclic anhydrides and mixed anhydrides, such as dialkylphosphoric acid mixed anhydrides, dialkylphosphorous acid mixed anhydride etc. Examples of activated esters as R$_1$, R$_2$, R$_3$ or R$_6$ include C$_{1-8}$alkyl ester, e.g. methyl ester or ethyl ester, cyanomethyl ester, p-nitrophenyl ester, an ester with N-hydroxysuccinimide, optionally ring-substituted phenyl or benzyl ester, or fluorenylmethyl ester. Examples of active carboxylic acid amides as R$_1$, R$_2$, R$_3$ or R$_6$ include amides with imidazole, dimethyl-imidazole or triazole. Carboxylic amide groups as R$_1$, R$_2$, R$_3$ or R$_6$ may also be e.g. —CONH$_2$, —CONHR$_a$ or —CONR$_a$R$_a$' as defined above.

Examples of functional derivatives of —SO$_3$H or —PO$_3$H are e.g. C$_{1-6}$ alkyl, benzyl, phenyl, allyl or trimethylsilyl esters, acid halides, e.g. acid chloride, or lower dialkyl amides, e.g. diethyl or diisopropyl amides. Preferred are (alkoxy)(diamino)phosphines, e.g. such a phosphine wherein "alcoxy" is methoxy, butoxy, allyloxy or benzoxy and "diamino" is diethylamino, dipropylamino or diisopropylamino.

R$_9$ in R$_6$ is preferably —NHR$_c$ wherein R$_c$ is a functional group capable of covalently reacting with an antigen, an antigenic group or

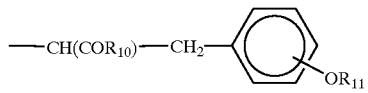

wherein R$_{10}$ is OH or C$_{1-8}$ alkoxy and R$_{11}$ is C$_{1-6}$ alkyl. OR$_{11}$ is preferably in para.

When R$_6$ is a COOH functional derivative, it may also be —CONHR$_c$ wherein R$_c$ is as defined above.

Examples of an anion X$_2^\ominus$ include e.g. OH$^\ominus$, Cl$^\ominus$, Br$^\ominus$, I$^\ominus$, CH$_3$COO$^\ominus$, CF$_3$COO$^\ominus$, citrate.

Suitable spacer groups as Z$_a$ or Y$_2$ include e.g. a radical of formula (b)

—R$_7$—X$_3$— (b)

wherein

X$_3$ is a divalent group derived from a functional moiety capable of covalently reacting with a protecting group or an antigen, and R$_7$ is C$_{1-6}$alkylene optionally interrupted by one or more heteroatoms or radicals selected from oxygen, sulfur, CO, —NHCO—, —CO—NH—, —N(C$_{1-4}$alkyl)—CO—, —CO—N(C$_{1-4}$alkyl)—, —NH— and —N(C$_{1-4}$alkyl)—; hydroxy substituted C$_{1-6}$alkylene; C$_{2-6}$ alkenylene;

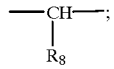

or a radical of formula (α$_1$)

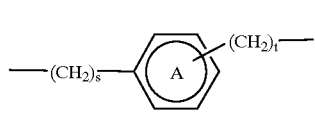

wherein each of s and t independently is 0, 1, 2 or 3, the ring A is optionally substituted and R$_8$ is an optionally protected residue as attached in C$_\alpha$ of a natural or non natural α-amino acid.

X$_3$ may be for example —CO—, —CS— or —NH—.

Examples of R$_8$ include e.g. an optionally N-protected residue as present e.g. on the C$_\alpha$ in Lys.

Suitable examples for the radical of formula (b) include e.g. succinyl, β-Ala or a divalent residue derived from 3-amino-propanoic acid, 3-aminoisobutanoic acid, 4-aminobutanoic acid, NH$_2$—C(CH$_3$)$_2$—COOH, 6-aminohexanoic acid, 1,8-diaminooctane, 1,6-diaminohexane or NH$_2$-(CH$_2$)$_{1-4}$—CO—NH—(CH$_2$)$_{1-6}$—NH$_2$.

Suitable groups capable of covalently reacting with an antigen or protecting group as Y$_a$ include e.g. a radical of formula (b$_1$)

 (b₁)

wherein
$R_7$ is as defined above, and
$X_4$ is carboxy, amino or a functional derivative thereof capable of reacting with an antigen or protecting group.

In the radical of formula (b₁) $R_7$ is preferably $C_{1-6}$ alkylene or $C_{2-6}$ alkenylene. When $R_c$ is a group capable of reacting with an antigen, it may have one of the significances given for $X_4$.

By antigenic group is meant a group derived from a carrier molecule e.g. as used in the preparation of antibodies, for example bovine serum albumin (BSA), ovalbumin, thyroglobulin, keyhole limpet hemocyanin or sepharose, or from an immunostimulant lipoamino acid or lipopeptide, e.g such compounds wherein the lipophilic moiety is tripalmitoyl, for example as disclosed by G. Jung and al in Int. J. Peptide Protein Res. 37, 1991, 46–57, herein incorporated by reference. Examples of lipopeptides are N-palmitoyl-S-[2,3-bis(palmitoyloxy)-(2RS)-propyl]-[R]-cysteine (referred to as Pam₃Cys-OH), Pam₃Cys-Ser, Pam₃Cys-Ser-(Lys)₄ and Pam₃Cys-Ser-(Glu)₄.

In the compounds of formula I, the following significances are preferred either individually or in any combination or sub-combination:

1. X is —(CH₂)n— wherein n is an integer from 2 to 8. More preferably n is 2.
2. Y is —(CH₂)m— wherein m is n−1. More preferably m is 1.
3. Z is —(CH₂)p— wherein p is an integer from 1 to 8. More preferably p is 2.
4. $R_4$ is OH.
5. $R_1$ is hydrogen, carboxy or a functional derivative thereof, primary, secondary or tertiary amino group, or a radical of formula (a), preferably a radical of formula (a).
6. $R_2$ is hydrogen, carboxy or a functional derivative thereof, primary, secondary or tertiary amino group, or a radical of formula (a), preferably a radical of formula (a).
7. $R_3$ is carboxy or a functional derivative thereof, primary, secondary or tertiary amino group, or a radical of formula (a). More preferably $R_3$ is a radical of formula (a).
8. The radical of formula (a) is

or a functional derivative thereof, wherein $R'_5$ is —NH₂ or —NHR$_a$, e.g. such a group wherein $R'_5$ is —NH₂, —NHY$_a$ or —NHZ$_a$—Y$_b$ and the carboxy is replaced by a functional derivative thereof, e.g. an ester or amide.

9. In the radical of formula (a) as indicated in 8. $R'_5$ is —NHZ$_a$—Y$_b$.
10. In the radical of formula (a) as indicated in 8., when $R'_5$ is —NHZ$_a$—Y$_b$, Y$_b$ is preferably an antigenic group, more preferably an antigenic group derived from bovine serum albumine or keyhole limpet hemocyanin or sepharose.
11. The radical of formula (a) is

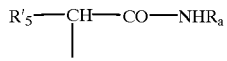

wherein $R'_5$ is NH₂ or NHY$_a$. $R_a$ is preferably Z$_a$—Y$_b$. Y$_b$ is preferably an antigenic group, more preferably an antigenic group derived from bovine serum albumine or keyhole limpet hemocyanin. Y$_a$ is preferably a protecting group.

12. The radical of formula (a) is

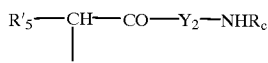

wherein $R'_5$ is NH₂ or NHY$_a$, Y₂ is a radical of formula (b) and $R_c$ is an antigenic group, more preferably an antigenic group derived from bovine serum albumine, keyhole limpet hemocyanin or sepharose. Y$_a$ is preferably a protecting group.

According to a preferred embodiment, the invention provides compounds of formula I wherein X is —CH₂—CH₂—, Y is —CH₂—, each of $R_1$ and $R_2$ is a residue of formula (a) wherein $R_5$ is —NH₂ or NHY'$_a$ wherein Y'$_a$ is a protecting group and $R_6$ is —COOH or $C_{2-9}$ alkoxycarbonyl, $X_1$ is H or OH, preferably H, Z is —CH₂—CH₂— and $R_3$ is a residue of formula (a) wherein $R_5$ is —NH₂ or NHY'$_a$ and $R_6$ is —CONH—Z$_a$—Y$_b$, —CONHY$_a$, —CONHR$_c$ or —CO—Y₂—NHR$_c$ wherein $R_c$ is an antigenic group, or

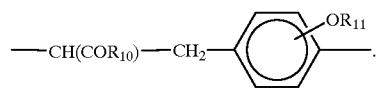

$R_4$ is OH.

According to another preferred embodiment, the invention provides compounds of formula I wherein X is —CH₂—CH₂—, Z is —CH₂—CH₂—, each of $R_1$ and $R_3$ is a residue of formula (a) wherein $R_5$ is —NH₂ or NHY'$_a$ and $R_6$ is —COOH or C₂9 alkoxycarbonyl, $X_1$ is H or OH, preferably H, Y is —CH₂— and $R_2$ is a residue of formula (a) wherein $R_5$ is —NH₂ or —NHY'$_a$ and $R_6$ is —CONH—Z$_a$—Y$_b'$ —CONHY$_a$, —CONHR$_c$ or —CO—Y₂—NHR$_c$ wherein $R_c$ is an antigenic group or

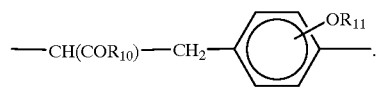

$R_4$ is OH.

According to a further preferred embodiment, the invention provides compounds of formula I wherein Z is —CH₂—CH₂—, Y is —CH₂—, each of $R_2$ and $R_3$ is a residue of formula (a) wherein $R_5$ is —NH₂ or NHY'$_a$ and $R_6$ is —COOH or $C_{2-7}$alkoxycarbonyl, $X_1$ is H or OH, preferably H, X is —CH₂—CH₂— and $R_1$ is a residue of formula (a) wherein $R_5$ is —NH₂ or —NHY'$_a$ and $R_6$ is —CONH—Z$_a$—Y$_b$, —CONHY$_a$, —CONHR$_c$ or —CO—Y₂—NHR$_c$ wherein $R_c$ is an antigenic group or

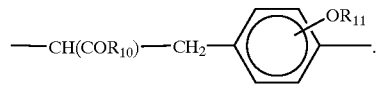

$R_4$ is OH.

The compounds of formulae I and IA may exist e.g. in salt form. Salts include acid addition salts with e.g. organic acids, polymeric acids or inorganic acids, for example hydrochloride and acetate, and salt forms obtainable with the carboxylic, sulfonic or phosphoric acid groups present in the molecule, e.g. alkali metal salts or substituted or unsubstituted ammonium salts and so-called internal salts when the molecule comprises at least one radical of formula (a).

The radical of formula (a) comprises an asymmetric carbon atom and may be present in D or L configuration. The compounds of formula I and IA also comprise an asymmetric carbon when $X_1$ is OH. The present invention is to be understood as embracing optical isomers as well as diastereoisomers of compounds of formula IA and compounds of formula I wherein $X_1$ is OH and up to three radicals of formula (a) are present in the molecule. Similar consideration apply in relation to starting materials comprising a radical of formula (a) or wherein $X_1$ is OH.

According to a specific embodiment of the invention, there is provided a compound of formula I'

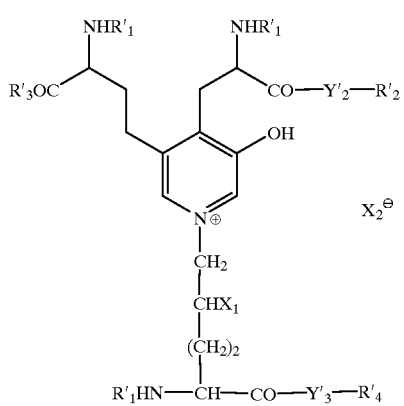

(I')

wherein $X_1$ and $X_2^\ominus$ are as defined above, each of $R'_1$ independently is an amino protecting group or $C_{1-8}$alkyl, $R'_3$ is OH or $C_{1-8}$alkoxy either $Y'_2$ is a direct bond, and $R'_2$ is OH or $C_{1-8}$alkoxy, $Y'_3$ is a direct bond or a spacer group and $R'_4$ is

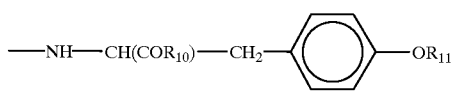

wherein $R_{10}$ and $R_{11}$ are as defined above, or $Y'_2$ is a direct bond, $R'_2$ is OH or $C_{1-8}$alkoxy, $Y'_3$ is a spacer group and $R'_4$ is bovine serum albumin (BSA) or sepharose or $Y'_2$ is a spacer group and $R'_2$ is bovine serum albumin or sepharose and $Y'_3$ is a direct bond and $R'_4$ is OH or $C_{1-8}$alkoxy.

The present invention also provides a process for the production of a compound of formula I or IA, which process comprises a) reacting a compound of formula II

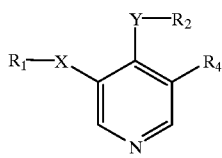

(II)

wherein X, Y, $R_1$, $R_2$ and $R_4$ are as defined above with a compound of formula III $$X_5\text{—}CH_2\text{—}CHX_1\text{—}Z\text{—}R_3 \quad (III)$$

wherein $X_1$, Z and $R_3$ are as defined above, and $X_5$ is a leaving group; or b) converting a compound of formula I or IA into another compound of formula I or IA and recovering a compound of formula I or IA thus obtained in free form or in salt form.

In the compounds of formula III, $X_5$ may be e.g. halogenide, optionally substituted ammonium, methane- or ethanesulfonate, tosylate. When $X_5$ is halogenide, it may be converted into an anion as $X_2^\ominus$.

Process step (a) may conveniently be carried out in an aprotic solvent, advantageously at a temperature from room temperature up to a temperature below the boiling point of the reaction mixture.

Process step (b) may be e.g. the removal of at least one protecting group from a compound of formula I in protected form or the introduction optionally through a spacer group of at least one protecting or antigenic group in a compound of formula I or IA free from a protecting or antigenic group or partially in protected form.

For the production of a compound of formula I comprising at least one antigenic group, a compound of formula IA or a compound of formula I wherein $R_3$ and/or $R_1$ and/or $R_2$ is carboxy, —$SO_3H$ or —$PO_3H$ or a functional derivative thereof, a primary or secondary amino group or a radical of formula (a) free from an antigenic group, is reacted with an antigen optionally through a spacer group.

In the case the protecting group or the antigenic group is attached through a spacer group, the reaction may alternatively be performed with the spacer group being already attached either to the compound of formula I or IA or to the protecting group yielding compound or antigen. Alternatively a compound of formula I may be reacted with a protecting group yielding compound or an antigen, each of the compound of formula I and the reactant comprising a spacer group which is complementary in order to obtain the desired spacer group $Z_a$ or $Y_2$.

The same considerations apply for the preparation of a compound of formula I wherein $Y_b$ is biotinyl or a group having a similar marking function.

Compounds of formula II, used as starting materials, are also novel and form part of the invention.

Compounds of formula II may be prepared by a process comprising i) removing at least one protecting group from or adding at least one protecting group to an amino group or a carboxy group of a compound of formula II, optionally through a spacer group; or ii) cyclizing a compound of formula IV

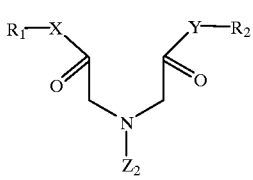

(IV)

wherein X, Y, $R_1$ and $R_2$ are as defined above, and $Z_2$ is a leaving group and, where required, etherifying a compound of formula II thus obtained wherein $R_4$ is OH into a compound of formula II wherein $R_4$ is alkoxy or polyalkylenoxy, and recovering a compound of formula II thus obtained in free form or in salt form.

Process step (i) may be carried out in accordance with known techniques.

Process step (ii) may conveniently be effected in an inert solvent, preferably at room temperature. Cyclization may advantageously be performed in the presence of a base, e.g. 1,5-diazabicyclo[4.3.0]non-5-ene (DBN) or 1,8-diazabicyclo[5.4.0]undec-7-ene (DBU).

Insofar the preparation of the starting materials is not particularly disclosed they may be produced in analogy to Example 4.

The following examples are illustrative of the invention. All temperatures are in °C. BOC=t.-butoxycarbonyl

EXAMPLE 1

3-Hydroxy-1-(5-t.-butoxycarbonylamino-5-t.-butoxycarbonyl-pentyl)-4-(1-t.-butoxycarbonylamino-1-t.-butoxycarbonyl-2-ethyl)-5-(3-t.-butoxy-carbonylamino-3-t.-butoxycarbonyl-propyl)-pyridinium iodide 2.0 g of 3-hydroxy-4-(1-t.-butoxycarbonylamino-1-t.-butoxycarbonyl-2-ethyl)-5-(3-t.-butoxycarbonylamino-3-t.-butoxycarbonyl-propyl)pyridine and 1.9 g t.-butyl 6-iodo-2-t.-butoxycarbonylamino-hexanoate in 25 ml dioxan are heated to 110° for 1 hour. After evaporation the title compound is isolated by column chromatography on silica gel (methylenchloride/methanol/ammonia 95:5:0.5).
MS (FAB): M$^+$ 881

EXAMPLE 2

3-Hydroxy-1-(5-amino-5-carboxy-pentyl)-4-(1-amino-1-carboxy-2-ethyl)-5-(3-amino-3-carboxy-propyl) pyridinium hydrochloride 206 mg of the title compound of example 1 are stirred in 20 ml trifluoracetic acid/water 95:5 for 90 min. By addition of diethyl ether crude title compound is precipitated and filtered. This mixture is dissolved in 2 ml methanol and acidified to pH=1 with 2N HClsolution in diethyl ether. After evaporation the residue is purified by preparative HPLC.
Column: Macherey/Nagel SA5/SCX 5 m 4.6×200 mm
Solvents: A: 0.02 M LiCl
B: 0.2 M LiCl
Gradient: A+0–100% B in 50 min.
Detection: UV 290 nm The fractions containing the title compound are desalted by passing through a Bio-Gel P2 column(50–100 mesh) eluting with water. After freeze-drying pure title compound is isolated.
MS (FAB): M$^+$ 413

EXAMPLE 3

2-t.-butoxycarbonylaminoamino-4-[3-hydroxy-4-(1-t.-butoxycarbonyl-1-amino-2-ethyl)-5-pyridinyl] butanoic acid t.-butyl ester 212 mg 1,13-di-t.-butyl 7-t.-butoxycarbonylaza-2,12-di-t.-butoxycarbonylamino-5,9-dioxo-tridecano-diate are dissolved in 10 ml tetrahydrofuran and 0.26 ml 1,8-diazabicyclo[5,4,0]-undec-7-en are added. This solution is stirred for 15 hours at room temperature and then evaporated. The mixture is separated by column chromatography on silica gel (methylene chloride/methanol 96:4), thus yielding the title compound.
MS (FAB): MH$^+$ 596

EXAMPLE 4

1,13-di-t.-butyl 7-t.-butoxycarbonylaza-2,12-di-t.-butoxycarbonylamino-5,9-dioxo-tridecano-diate, used as starting material in Example 3 may be prepared as follows:
a) T.-butyl 2-t.-butoxycarbonylamino-5,6-epoxy-hexanoate 13.1 g m-chloroperoxybenzoic acid (90%) are added to 13.8 g t.-butyl 2-t.-butoxycarbonylamino-5-hexenoate dissolved in 400 ml methylene chloride. After 18 hours stirring at room temperature the mixture is treated with ice/sat. NaHCO$_3$ solution. The aqueous part is extracted twice with methylene chloride. The organic solutions are combined, dried and evaporated. Chromatography on silica gel using ethyl acetate/hexane 1:2.5 yields the title compound 4a).
MS (FAB): MH$^+$ 286 b) 1,13-Di-t.-butyl 7-N-benzylaza-5,9-dihydroxy-2,12-di-t.-butoxy-carbonylamino-tridecano-diate A mixture of 1 g of title compound 4a) and 0.18 ml benzylamine is heated to 70° for 18 hours. This mixture is separated by column chromatography on silica gel (acetone/hexane 1:2), thus yielding the title compound 4b).
MS (FAB): MH$^+$ 710 c) 1,13-Di-t.-butyl 7-aza-5,9-dihydroxy-2,12-di-t.-butoxycarbonylamino-tridecano-diate 9.48 g of the title compound 4b) are dissolved in 350 ml ethanol and hydrogenated in the presence of 1.4 g 10% Pd on charcoal at room temperature and normal pressure. This mixture is then filtered and evaporated. The title compound 4c) is purified by column chromatography on silica gel (methylene chloride/methanol 9:1)
MS (FAB): MH$^+$ 620 d) 1,13-Di-t.-butyl 7-tert.butoxycarbonylaza-5,9-dihydroxy-2,12-di-t.-butoxycarbonylamino-tridecano-diate 4.1 g di-t.-butyl dicarbonate are quickly added to 7.7 g of the title compound 4c) dissolved in 310 ml tetrahydrofuran. The resulting solution is stirred for 3 hours at room temperature. After evaporation the title compound 4d) is purified by column chromatography on silica gel (hexane/ethyl acetate 6:4)
MS (FAB): MH$^+$ 720 e) 1,13-Di-t.-butyl 7-t.-butoxycarbonylaza-2,12-di-t.-butoxycarbonylamino-5,9-dioxo-tridecano-diate A solution of 4.0 ml dimethyl sulfoxide in 42 ml methylene chloride is added dropwise at –70° to a solution of 140 ml methylene chloride and 2.4 ml oxalyl chloride. After 15 min. a mixture of 8.0 g of the title compound 4d) in 80 ml methylene chloride is added slowly at –700 to the solution. After 3 hours stirring at –70°, 15.7 ml triethylamine are added at –50°. This mixture is then poured on ice/water. The fractions are separated and the aqueous part is extracted twice with diethyl ether. All organic fractions are combined, dried and evaporated. The residue is purified by column chromatography on silica gel (hexane/ethyl acetate 6:4), thus yielding pure title compound 4e).
MS (FAB): MH$^+$ 716

EXAMPLE 5

3-Hydroxy-1-(2-hydroxy-5-amino-5-carboxy-pentyl)-4-(1-amino-1-carboxy-2-ethyl)-5-(3-amino-3-carboxy-propyl) pyridinium hydrochloride The procedures of Examples 1 and 2 are repeated using t.-butyl-5-hydroxy-6-iodo-2-t.-butoxycarbonylamino-hexanoate.
MS (FAB): M$^+$ 429

3-Hydroxy-1-(2-hydroxy-5-t.-butoxycarbonylamino-5-t.-butoxycarbonyl-pentyl)-4-(1-t.-butoxycarbonylamino-1-t.-butoxycarbonyl-2-ethyl)-5-(3-t.-butoxycarbonylamino- 3-t.-butoxycarbonyl-propyl)-pyridinium iodide
MS (FAB): M$^+$ 897

EXAMPLE 6

3-Hydroxy-1-[5-t.-butoxycarbonylamino-5-N-(1-methoxycarbonyl-2-ethyl)carboxamido-pentyl]-4-(1-t.-butoxycarbonylamino-1-t.-butoxycarbonyl-2-ethyl)-5-(3-t.-butoxycarbonylamino-3-t.-butoxycarbonylpropyl)-pyridinium iodide.

235 mg of the compound of Example 3 and 230 mg of εiodo-N-t.-butoxycarbonylamino-(methyl-β alanyl)lysin in 1 ml dioxan are heated to 120° for 30 minutes. After evaporation the title compound is purified by chromatography on silica gel (ethyl acetate/methanol 7:3).
MS-FAB: M$^+$ 910

EXAMPLE 7

3-Hydroxy-1-[5-t.-butoxycarbonylamino-5-N-(1-carboxy-2-ethyl)carbo-xamido-pentyl]-4-(1-t.-butoxycarbonylamino-1-t.-butoxycarbonyl-2-ethyl)-5-(3-t.-butoxycarbonylamino-3-t.-butoxycarbonyl-propyl)-pyridinium hydroxide.

50 mg of the title-compound of Example 6 are dissolved in 5 ml methanol and 2 ml of 0.2 N sodium hydroxide and stirred for 5 hours at room temperature. Then 10 ml water and 10 ml methylene chloride are added and, under vigourous stirring, 0.2 N hydrochloric acid is added until pH=2–3. The organic layer is separated, dried over sodium sulphate and evaporated. Chromatography on silica gel (methylene chloride/methanol 6:4) yields the title compound.

MS-FAB: M$^+$ 896

EXAMPLE 8

45 of the compound of Example 7 is dissolved in 1 ml N,N-dimethylformamide and 12 mg 1-hydroxybenzotriazole followed by 13 µl diisopropyl-ethylamine (Huenig Base), 32 mg N-biotinyl-1,4-diaminobutane in 2 ml N,N-dimethyl-formamide, 15 mg N,N-dicyclohexylcarbodiimide are added. This mixture is stirred at room temperature for 23 hours. After evaporation and chromatography on silica gel (methylene chloride/methanol/ammonia 90/10/1) the title compound is isolated.

MS-FAB: M$^+$ 1192

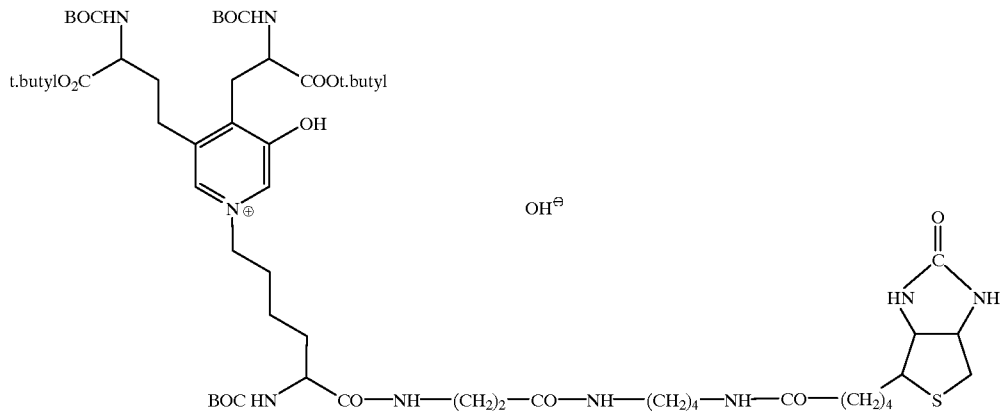

EXAMPLE 9

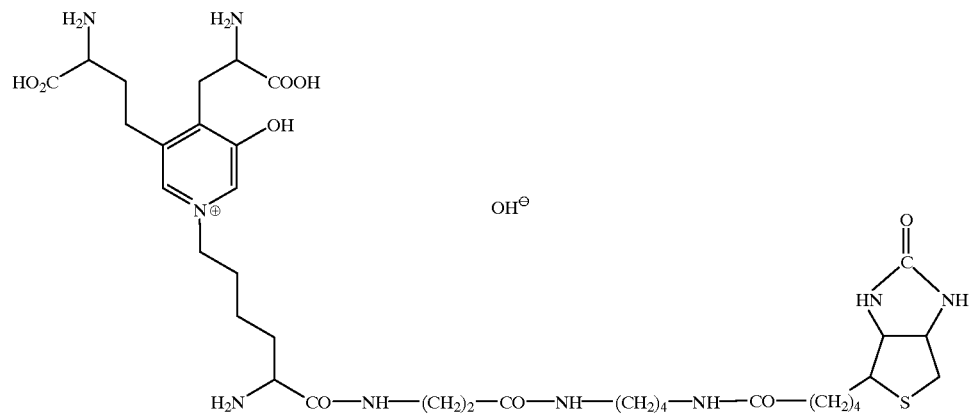

128 mg of the compound of Example 8 is dissolved in 25 ml trifluoroacetic acid/water 95:5 and stirred for 1 hour at room temperature. The solvents are evaporated and the residue purified by HPLC.
Column: Hypersil ODS 4.6×250 mm
Solvents: A: 100% H20, 1% CF3COOH
B: 80% CH3OH, 20% H20 , 1% CF3COOH
Gradient: A +20% B for 20 minutes
MS-FAB: M$^+$ 780

EXAMPLE 10
Desoxypyridinolin-1-β-alanyl-BSA-Conjugate 14 mg of the compound of Example 7 is dissolved in 0.4 ml N,N-dimethyl-formamide, then 3.3 mg N-ethyl-N-(3-dimethylaminopropyl)-carbodiimide hydrochloride followed by 2.3 mg N-hydroxy-succinimide are added. This solution is stirred for 2 hours at room temperature, then 65 mg bovine serum albumin (BSA) in 2 ml phosphate buffer (pH=8) are added and stirring is continued for 6 hours. Then solvents are evaporated and the residue is dissolved in 10 ml trifluoroacetic acid/water 95:5 and stirred for 90 minutes at room temperature. After evaporation the residue is purified by chromatography on Bio-Gel P 6 (100–200 mesh) water/acetic acid 98:2. The "high" molecular part is collected and used for immunisation.

EXAMPLE 11
Desoxypyridinolin-1-β-alanyl-KLH-Conjugate 2.5 mg of the compound of Example 7 are dissolved in 2.5 ml N,N-dimethyl-formamide, then 0.7 mg N-ethyl-N-(3-dimethylaminopropyl)-carbodiimide hydrochloride followed by 0.5 mg N-hydroxy-succinimide are added. This mixture is stirred for 90 minutes at room temperature. Then 34.2 mg hemocyanin from keyhole limpets (KLH) in 0.5 ml 50% glycerol is added and stirring is continued at room temperature for 36 hours. Then 5 ml trifluoroacetic acid/water 95:5 are added and the solution stirred for 75 minutes at room temperature. Trifluoroacetic acid and water are removed by evaporation. The residue is washed (centrifuged) several times with water and then used for immunisation.

EXAMPLE 12
3-Hydroxy-4-(2-t.-butoxycarbonylamino-2-carboxy-ethyl)-5-(3-t.-butoxy-carbonylamino-3-t.-butoxycarbonyl-propyl)-pyridine 0.5 g of the compound of Example 3 is dissolved in 10 ml water and 10 ml methanol and 1 g sodium hydroxide is added. The resulting solution is stirred for 3 hours at room temperature. and then worked up as disclosed in Example 8.
MS-FAB: MH$^+$ 540

EXAMPLE 13
3-Hydroxy-4-[1-t.-butoxycarbonylamino-1-N-(1-ethyl-methoxycarbonyl)-carboxamido-2-ethyl]-5-(3-t.-butoxycarbonylamino-3-t.-butoxycarbonyl-propyl)-pyridine 320 mg of the compound of Example 12, 200 mg 1-hydroxybenzotriazole, 300 mg N,N-dicyclohexylcarbodiimide, 200 mg βalanine methyl ester are dissolved in 10 ml tetrahydrofuran and stirred overnight at room temperature. After evaporation of the solvent, the residue is purified on silica gel (methylene chloride/methanol 95:5).
MS-FAB: MH$^+$ 625

EXAMPLE 14
3-Hydroxy-1-(5-t.-butoxycarbonylamino-5-t.-butoxycarbonyl-pentyl)-4-[1-t.-butoxycarbonylamino-1-N-(1-methoxycarbonyl-2-ethyl)carbo-xamido-2-ethyl]-5-(3-t.-butoxycarbonylamino-3-t.-butoxycarbonyl-propyl)-pyridinium iodide.

This compound is prepared as disclosed in Example 1.
MS-FAB: M$^+$ 910

EXAMPLE 15
3-Hydroxy-1-(5-t.-butoxycarbonylamino-5-t.-butoxycarbonyl-pentyl)-4-[1-t.-butoxycarbonylamino-1-N-(1-carboxy-2-ethyl)-carboxamido-2-ethyl]-5-(3-t.-butoxycarbonylamino-3-t.-butoxycarbonyl-propyl)-pyridinium hydroxide This compound is prepared by following the procedure of Example 7.
MS-FAB: M$^+$ 896

EXAMPLE 16
The title compound of Example 15 is coupled to BSA or KLH in the same way as described in Examples 10 and 11. The resulting compounds have either BSA or KLH attached to the carboxy group of the lateral chain in position 4 of the pyridinium ring, respectively.

EXAMPLE 17
2-amino-4-[3-hydroxy-4-(1-carboxy-1-amino-2-ethyl)-5-pyridinyl] butanoic acid 200 mg of the compound of Example 3 are treated with 20 ml of trifluoroacetic acid/water 95:5 for 90 min. then evaporated.
MS (FAB): MH$^+$ 284

EXAMPLE 18

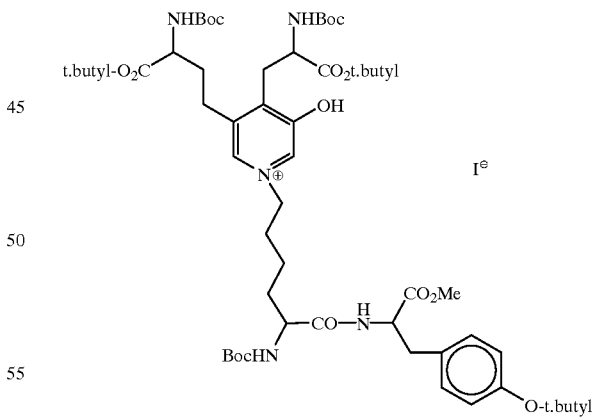

The procedure of Example 6 is repeated. 100 mg of the compound of Example 3 and 120 mg (epsilon-iodo-N-t.-butoxycarbonylamino-(methyl-0-t.-butyl-tyrosinyl)lysine are heated in 1 ml 1,4-dioxan to 1200 for 1 hour. After evaporation the compound is purified by chromatography on silica gel (methylene chloride/methanol 95:5).

MS-FAB: M$^+$ 1058

EXAMPLE 19

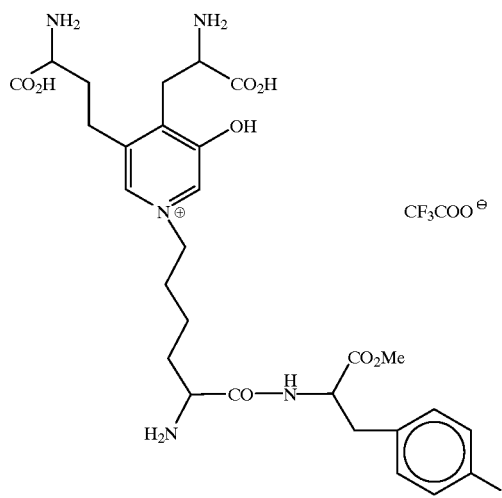

18.4 mg of the compound of Example 18 is dissolved in 2 ml trifluoroacetic acid/water 95:5 and stirred for 2 hours at room temperature. The compound is isolated by precipitation with diethyl ether and dried after filtration over night.
MS-FAB: M$^+$ 590

EXAMPLE 20

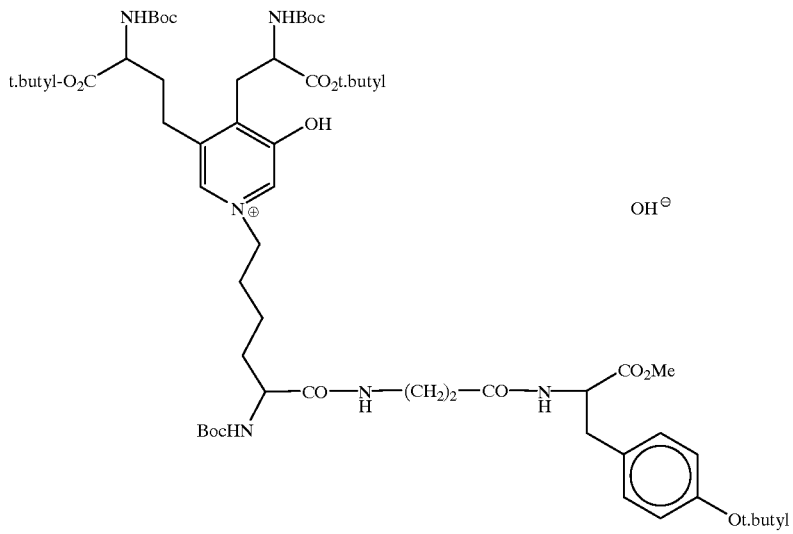

30 mg of the compound of Example 7 is dissolved in 1 ml N,N-dimethyl-formamide and 11.7 mg 1-hydroxybenzotriazole followed by 25 µl diisopropyl-ethylamine (Huenig Base), 21 mg 0-t.-butyl-tyrosine methyl ester hydrochloride, 15 mg N,N-dicyclohexylcarbodiimide are added. This mixture is stirred at room temperature for 48 hours. After evaporation and chromatography on silica gel (methylene chloride/methanol/ammonia 90/10/1) the above indicated compound is isolated.

MS-FAB: M$^+$ 1129

EXAMPLE 21

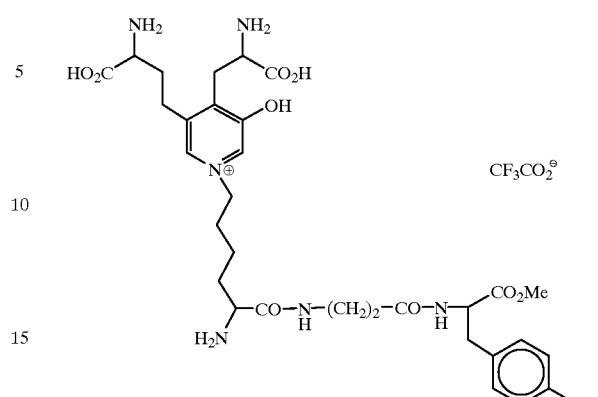

17 mg of the compound of Example 20 is dissolved in 2 ml trifluoroacetic acid/water 95:5 and stirred for 75 minutes at room temperature. The compound is isolated by precipitation with diethyl ether and dried after filtration over night.

MS-FAB: M$^+$ 661

EXAMPLE 22

Desoxypyridinolin-4-0-alanyl-BSA-conjugate

This conjugate is prepared in analogy with the procedure described in Example 10 using as starting material, 3-hydroxy-1-(5-t.-butoxycarbonylamino-5-t.-butoxycarbonylpentyl)-4-[1-t.-butoxycarbonylamino-1-N-(1-carboxy-2ethyl)-carboxamido-2-ethyl]-5-(3t.-butoxycarbonylamino-3 -t.butoxycarbonyl-propyl)-pyridinium hydroxide.

EXAMPLE 23

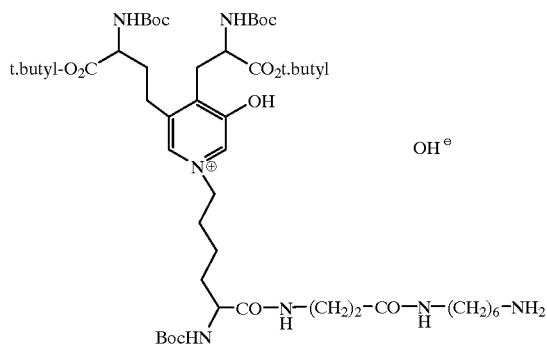

50 mg of the compound of Example 7 is dissolved in 1 ml N,N-dimethyl-formamide and 13.1 mg 1-hydroxybenzotriazole followed by 17.3 mg N,N-dicyclohexylcarbodiimide, 27 mg 6-amino-1-fluoren-9-ylmethoxy-carbonylamino-hexan trifluoracetate (triflate) dissolved in a mixture of 1 ml of N,N-dimethylformamide and 27 µl diisopropyl-ethylamine (Huenig Base), are added. This mixture is stirred at room temperature for 24 hours and then evaporated. The residue is dissolved in 1 ml N,N-dimethylformamide/piperidine 8:2 and stirred for 30 minutes. After evaporation and chromatography on silica gel (methylene chloride/methanol/ammonia 85/15/1.5) the above indicated compound is isolated.

MS-FAB: M$^+$ 994

EXAMPLE 24

3-Hydroxy-1-[15-t.butoxycarbonylamino-2-hydroxy-5-N-(1-methoxy-carbonyl-2-ethyl)carboxamido-pentyl]-4-(1-t.-butoxycarbonylamino-1-t.-butoxycarbonyl-2-ethyl)-5-(3-t.-butoxycarbonylamino-3-t.-butoxy-carbonyl-propyl)-pyridinium iodide 120 mg of the compound of Example 3 and 130 mg of 6-iodo-5-hydroxy-N-t.-butoxycarbonylamino-(methyl-g-alanyl)lysin are coupled and purified following the procedure described in Example 6.

MS-FAB: M$^+$ 926

EXAMPLE 25

3-Hydroxy-1-[5-t.butoxycarbonylamino-2-hydroxy-5-N-(1-carboxy-2-ethyl)carboxamido-pentyl]-4-(1-t.-butoxycarbonylamino-1-t.-butoxycarbonyl-2-ethyl)-5-(3-t.-butoxycarbonylamino-3-t.-butoxycarbonyl-propyl)-pyridinium hydroxide.

The title compound is prepared following the procedure described in Example 7.

MS-FAB: M$^+$ 912.

EXAMPLE 26

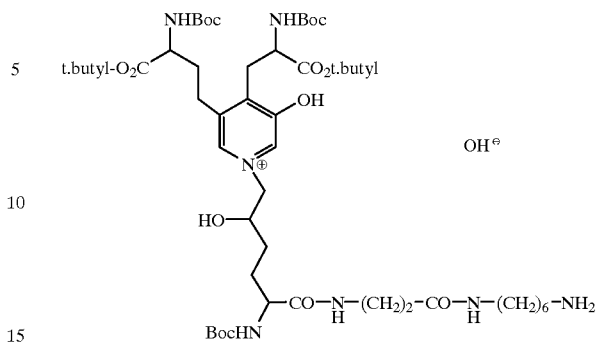

45 mg of the compound of Example 25 and 26 mg 6-amino-1-fluoren-9-ylmethoxycarbonylamino-hexan triflate are coupled following the procedure given in Example 23. After deprotection (N,N-dimethyl-formamide/piperidine 8:2, 30 minutes) and chromatography (methylene chloride/methanol/ammonia 85/15/1.5) the above compound is isolated.

MS-FAB: M$^+$ 1010

EXAMPLE 27

Desoxypyridinolin-1-[β-Ala—NB]—(CH$_2$)$_6$—NH-Sepharose 4B-Conjugate 15 mg of the compound of Example 23 is coupled to 1 g Sepharose 4B in analogy with the procedure disclosed in *Methods Enzymol.* 34, 13 (1974).

1. 1 g Bromocyan activated Sepharose 4B is treated with 1 mM hydrogen chloride.
2. 15 mg of the compound of Example 23 is dissolved in bicarbonate buffer (0.1 M; pH 8.3) containing 0.5 N sodium chloride.
3. The gel suspension (1.) and buffer solution (2.) are mixed and shaked at room temperature for 2 hours.
4. The mixture (3.) is treated with 1 M ethanolamine for 2 hours, and then with trifluoroacetic acid/water 95:5 for 2 hours. The resulting gel suspension is washed alternately with acetate buffer (0.1 M; pH 4) and bicarbonate buffer (0.1 M; pH 8.3) each containing 0.5 M sodium chloride; 4 times.

EXAMPLE 28

Pyridinolin-1-[β-Ala-NH—(CH$_2$)$_6$—NH]-Sepharose 4B-Conjugate 15 mg of the compound of Example 26 is coupled to 1 g Sepharose 4B in analogy with the procedure of Example 27.

Compounds of formulae I and IA are useful in assessing the levels of pyridinoline or deoxypyridinoline crosslinks derived from collagen degradation which are present in biological fluids, e.g. urine or serum. Conditions in humans and animals which are characterized by a high level of bone resorption or by an abnormal balance between bone formation and bone resorption are e.g. osteoporosis, Paget's disease, progress of begnin or malignant tumors of bone and metastatic cancers, osteomalacia, primary hyperparathyroidism, therapies with a compound increasing bone resorption (e.g.glucocorticoids), osteoarthritis and rheumatoid arthritis.

The quantitating of these crosslink levels may be carried out using e.g. immunological methods, electrochemical titration, natural fluorescence spectroscopy or ultraviolet absorbance. These methods may be conducted directly upon a body fluid without further purification or after purification, e.g. if there are excessive quantities of contamination substances. Free crosslinks present in biological fluids or crosslinks liberated by hydrolysis from collagen degradation peptides and present in body fluids may be quantitated according to the invention. By total crosslink is meant the total amount or concentration of free crosslink and hydrolyzed crosslink present in the body fluid.

Preferably the quantitation of pyridinoline or deoxypyridinoline cross-links in biological fluids is performed using immunological methods. Accordingly specific antibodies are prepared to compounds of formula I bearing at least one antigenic group referred to hereinafter as immunogen. Either polyclonal or monoclonal antibodies immunoreactive with a compound of formula I bearing at least one antigenic group and wherein $X_1$ is hydrogen and/or such a substituted compound wherein $X_1$ is hydroxy may be prepared. According to a preferred embodiment of the invention, specific antibodies immunoreactive with a compound of formula I bearing at least one antigenic group and wherein $X_1$ is H are prepared. Preferred antibodies are those raised against a compound of formula I wherein X is —$CH_2CH_2$—, Y is —$CH_2$—, each of $R_1$ and $R_2$ is a residue of formula (a) wherein $R_5$ is —$NHY'_a$ wherein $Y'_a$ is a protecting group and $R_6$ is $C_{2-9}$alcoxy carbonyl, $X_1$ is H or OH, preferably H, $R_4$ is OH, Z is —$CH_2$—$CH_2$- and $R_3$ is a residue of formula (a) wherein $R_5$ is —$NHY'_a$ and $R_6$ is —$CONHR_c$ or —CO—$Y_2$—$NHR_c$ wherein $R_c$ is antigenic group, preferably BSA.

As mentioned above, in the compounds of formula I the antigenic group may be attached directly or indirectly at a defined position: for example the antigenic group may be present in $R_1$, $R_2$ or $R_3$, particularly in $R_3$ or $R_2$. Preferably the antigenic group is attached through a spacer group. Compounds of formula IA produced according to the process of the invention are also useful to prepare a corresponding compound of formula I bearing one, two or three antigenic groups as disclosed above.

Antibody production may be effected by conventional techniques including injection of a compound of formula I bearing at least one antigenic group into suitable mammalian subjects such as mice, rabbits or sheep according to immunological techniques generally known in the art (Laboratory Techniques in Biochemistry and Molecular Biology, Campbell, A. M., 1986, 13, Elsevier). Sera are titrated to determine antibody formation with respect to the immunogen. Spleen cells or peripheral blood lymphocytes may be harvested, homogenized and thereafter fused with e.g. cancer cells to produce a fused cell hybrid which produces monoclonal antibodies immunoreactive with the desired crosslink compound of formula I according to the invention. Monoclonal antibody preparation may be carried out in accordance with techniques disclosed in G. Galfre and C. Milstein, 1981, Meth. Enzymol. 73,1 and in U.S. Pat. No. 4,634,664 and U.S. Pat. No. 4,634,666, which are incorporated herein by reference.

Polyclonal or especially monoclonal antibodies or fragments thereof produced by the above procedures or equivalent procedures may be employed in various immunometric assays to quantitate the concentration of pyridinoline or deoxypyridinoline crosslinks derived from collagen degradation in biological fluids. These immunometric assays comprise a monoclonal antibody or antibody fragment coupled to a detectable marker. Examples of suitable detectable markers include e.g. enzymes, coenzymes, enzyme inhibitors, chromophores, fluorophores, chemiluminescent materials, paramagnetic metals, spin labels and radionuclides. Examples of standard immunometric methods suitable for indexing bone resorption include e.g. enzyme linked immunosorbent assay (ELISA), radioimmunoassay (RIA) and sandwich immuno radiometric assay (IRMA).

A compound of formula I free from antigenic group, e.g. wherein X is —$CH_2CH_2$—, Y is —$CH_2$—, each of $R_1$ and $R_2$ is

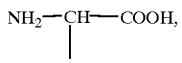

R is OH, X is H or OH, Z is —$CH_2CH_2$—, $R_3$ is

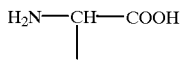

and $X_2^\ominus$ is an anion other than $Cl^\ominus$ or $CH_3CO_2^\ominus$, or a compound of formula IA prepared according to the invention wherein $X_1$ is H or OH can be used as standard references for quantitating the concentration of pyridinoline or deoxypyridinoline crosslinks derived from collagen degradation in a biological fluid e.g. in any of the above mentioned quantitating method or kit based on such a quantitating method.

Compounds of formula I' of the type as disclosed in Example 19 or 21, e.g. with a tyrosine residue can be labelled with radioactive iodine and accordingly be used as a "tracer" for quantitative and qualitative immunodetection of the desired antibodies to pyridinoline or deoxypyridinoline crosslinks. Compounds of formula I' of the type as disclosed in Example 27 or 28 are useful for the purification of the desired antibodies, e.g. according to known methods, e.g. affinity chromatography. Compounds of formula I' of the type as disclosed in Example 22 are useful as antigens for the production of polyclonal and monoclonal antibodies as disclosed above.

In accordance with the foregoing, the present invention provides

1. A method of determining connective tissue metabolism abnormalities, e.g. bone or cartilage resorption by quantitating the concentration of total or free pyridinoline or deoxypyridinoline crosslinks derived from collagen degradation in a biological fluid, which method comprises using a compound of formula I;
2. A method of determining connective tissue metabolism abnormalities, e.g. bone or cartilage resorption by quantitating the concentration of total or free pyridinoline or deoxypyridinoline crosslinks derived from collagen degradation in a biological fluid, which method comprises using a compound of formula IA as produced by the process of the invention;
3. A method of quantitating the concentration of total or free pyridinoline or deoxypyridinoline crosslinks derived from collagen degradation in a biological fluid, which method comprises contacting the biological fluid with specific polyclonal or monoclonal antibodies immunoreactive with a compound of formula I bearing at least one antigenic group and wherein $X_1$ is H or OH, preferably a compound of formula I as indicated above;
4. Use of a compound of formula IA as produced by the process of the invention or of a compound of formula I free from antigenic group as a standard for quantitating the concentration of total or free pyridinoline or deoxypyridinoline crosslinks derived from collagen degradation in a biological fluid;
5. Polyclonal or monoclonal antibodies as disclosed above;
6. A cell line which secretes said monoclonal antibodies;

7. A method to produce said monoclonal antibodies;

8. A kit for immunoassay determination of the amount or concentration of total or free pyridinoline or deoxypyridinoline crosslinks derived from collagen degradation in a biological fluid, comprising a composition containing an antibody or immunologically reactive fragment thereof as disclosed above, and an additional reagent for conduct of said immunoassay along with instructions for the conduct of said assay, using as standard a compound of formula IA prepared according to the process of the invention or a compound of formula I free from an antigenic group, wherein $X_1$ is H or OH, particularly H.

What is claimed is:

1. A compound of formula I

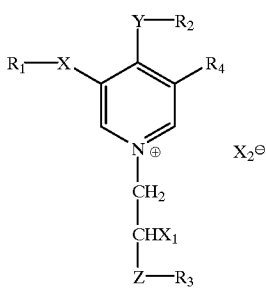

(I)

wherein X is —$CH_2$—$CH_2$—, Y is

—$CH_2$—, each of $R_1$ and $R_2$ is a residue of formula (a)

(a)

wherein $R_5$ is —$NH_2$ or $NHY'_a$ wherein $Y'_a$ is a protecting group and $R_6$ is —COOH or $C_{2-9}$alkoxy carbonyl, $X_1$ is H or OH, Z is —$CH_2$—$CH_2$— and $R_3$ is a residue of formula (a) wherein $R_5$ is —$NH_2$ or $NHY'_a$ and $R_6$ is $CONHR_c$ or —CO—$Y_2$—$NHR_c$ wherein $Y_2$ is a spacer and $R_c$ is an antigenic group or

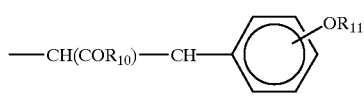

wherein $R_{10}$ is OH or $C_{1-8}$alkoxy and $R_{11}$ is $C_{1-6}$alkyl, or wherein X is —$CH_2$—$CH_2$—, Y is —$CH_2$—, Z is —$CH_2$—$CH_2$—, each of $R_1$ and $R_3$ is a residue of formula (a) wherein $R_5$ is —$NH_2$ or $NHY'_a$ and $R_6$ is —COOH or $C_{2-9}$alkoxycarbonyl, $X_1$ is H or OH, and $R_2$ is a residue of formula (a) wherein $R_5$ is —$NH_2$ or $NHY'_a$, and $R_6$ is —$CONHR_c$ or —$COY_2$—$NHR_c$ as defined above, $R_4$ being OH; and $X_2$ is an anion which is acetate, chloride, or iodide, provided that the compound of formula I is not hydroxylysyl pyridinoline or lysyl pyridinoline.

2. A process for the preparation of a compound of formula

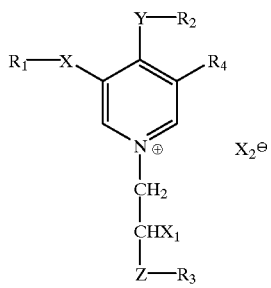

(I)

in which X is —$CH_2$—$CH_2$—, Y is —$CH_2$—, each of $R_1$ and $R_2$ is a residue of formula (a) wherein $R_5$ is —$NH_2$— or $NHY_a'$, wherein $Y_a'$ is an amine protecting group and $R_6$ is —COOH or $C_{2-9}$alkoxy carbonyl, $X_1$ is H or OH, Z is —$CH_2$—$CH_2$ and $R_3$ is a residue of formula (a) wherein $R_5$ is —$NH_2$— or $NHY_a'$ and $R_6$ is —$CONHR_c$ or —CO—$Y_2$—$NHR_c$ wherein $Y_2$ is a spacer and $R_c$ is an antigenic group or

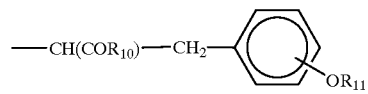

wherein $R_{10}$ is OH or $C_{1-8}$alkoxy and $R_{11}$ is $C_{1-4}$alkyl, or wherein X is —$CH_2$—$CH_2$—, Y is —$CH_2$—, Z is —$CH_2$—$CH_2$—, each of $R_1$ and $R_3$ is a residue of formula (a) wherein $R_5$ is —$NH_2$— or $NHY_a'$, and $R_6$ is —COOH or $C_{2-7}$alkoxycarbonyl, $X_1$ is H or OH, and $R_2$ is a residue of formula (a) wherein $R_5$ is —$NH_2$— or $NHY_a'$ and $R_6$ is —$CONHR_c$ or —CO—$Y_2$—$NHR_c$ as defined above and $R_4$ is OH;

which comprises a) cyclizing a compound of formula

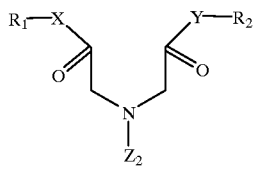

(IV)

in a basic solution to obtain a compound of formula II

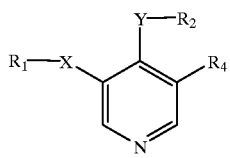

where X, Y, $R_1$, and $R_2$, are as defined above;
$Z_2$ is a leaving group; and
$R_4$ is hydroxy; and
b) reacting the compound of formula II with a compound of formula III

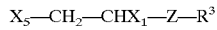

wherein $X_1$, Z and $R_3$, are as defined above, and $X_5$ is a leaving group; and $X_2$ is an anion which is acetate, chloride, or iodide.

3. A process according to claim 2 in which the spacer group $Z_a$ or $Y_2$ is selected from succinyl or a divalent residue derived from 3-aminopropanoic acid, 3-aminoisobutanoic acid, 4-aminobutanoic acid, $NH_2—C(CH_3)_2—COOH$, 6-aminohexanoic acid, 1,8-diaminooctane, 1,6-diaminohexane and $NH_2—(CH_2)_{1-4}—CO—NH—(CH_2)_{1-6}—NH_2$.

4. A process according to claim 2 in which the compound of formula I is 3-hydroxy-1-(5-t-butoxycarbonylamino-5-t-butoxycarbonyl-pentyl)-4-(1-t-butoxycarbonylamino-1-t-butoxycarbonyl-2-ethyl)-5-(3-t-butoxycarbonylamino-3-t-butoxycarbonyl-propyl)-pyridinium iodide.

5. A process according to claim 2 in which the compound of formula I is a 3-hydroxy-1-(5-amino-5-carboxy-pentyl)-4-(2-amino-2-carboxy-ethyl)-5-(3-amino-3-carboxy-propyl)-pyridinium chloride.

6. A process according to claim 2 in which the basic solution in step a) is a solution of 1,5-diazabicyclo [4.3.0] non-5-ene or a solution of 1,8-diazabicyclo [5.4.0] undec-7-ene.

7. A process according to claim 2 in which the cyclization is carried out in an inert solvent at room temperature.

8. A process according to claim 2 in which the compound of formula II is 2-t-butoxycarbonylamino-4-[3-hydroxy-4-(1-t-butoxycarbonyl-1-t-butoxycarbonylamino-2-ethyl)-5-pyridinyl] butanoic acid, t-butyl ester.

* * * * *